United States Patent [19]

Noda et al.

[11] 4,337,270
[45] Jun. 29, 1982

[54] NOVEL ANTHRANILIC ACID DERIVATIVES

[75] Inventors: Kanji Noda, Chikushino; Akira Nakagawa, Tosu; Toshiharu Motomura, Tosu; Masayoshi Tsuji, Tosu; Hidetoshi Amano, Tosu; Hiroyuki Ide, Fukuoka, all of Japan

[73] Assignee: Hisamitsu Pharmaceutical Co., Inc., Tosu, Japan

[21] Appl. No.: 152,217

[22] Filed: May 21, 1980

[51] Int. Cl.³ .................. A61K 31/245; C07C 101/72
[52] U.S. Cl. .................................... 424/310; 424/230; 424/309; 424/319; 560/21; 560/45; 560/46; 562/435; 562/452; 562/453; 562/455
[58] Field of Search ............................. 560/21, 45, 46; 562/435, 452, 453, 455; 424/230, 309, 310, 319

[56] References Cited

U.S. PATENT DOCUMENTS 3,674,844  7/1972  Shen et al. ............................. 560/45
3,814,772  6/1974  Philippe et al. ..................... 562/435
3,940,422  2/1976  Harita et al. .................... 260/501.11
4,026,896  5/1977  Harita et al. ........................ 562/455

OTHER PUBLICATIONS

Kamijo et al., Chem. Absts., 88, 6568(e) and 6569(f), 1978.

Harita et al., Chem. Absts., 81, 135741(k), 1974.

Primary Examiner—G. T. Breitenstein
Attorney, Agent, or Firm—Jordan and Hamburg

[57] ABSTRACT

Novel anthranilic acid derivatives of the general formula:

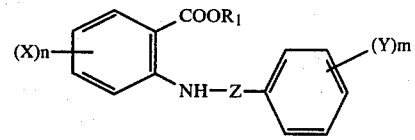

wherein X is a halogen atom, an alkoxyl group having 1-3 carbon atoms, an alkyl group having 1-3 carbon atoms or a nitro group, n is an integer of 1-2, Y is an alkoxyl group having 1-3 carbon atoms, m is an integer of 2-3, Z is —COCH=CH— or —CO—, $R_1$ is a hydrogen atom or an alkyl group having 1-4 carbon atoms, and pharmaceutically acceptable salts thereof, which derivatives and salts possess a strong antiallergic action and are thus useful as therapeutically active agents for diseases caused by allergies, such as asthma, hay fever, urticaria and atopic dermatitis; an antiallergic composition comprising the same; and a method of alleviating diseases caused by allergies using the same.

25 Claims, No Drawings

NOVEL ANTHRANILIC ACID DERIVATIVES

BACKGROUND OF THE INVENTION

1. Field of the Invention

This invention relates to novel anthranilic acid derivatives exhibiting an extremely strong antiallergic activity when administered orally to mammals including human beings. More particularly, this invention relates to anthranilic acid derivatives inhibiting anaphylaxis caused by an antigen-antibody reaction.

2. Description of the Prior Art

Disodium chromoglicate is well known as the only one drug that inhibits the disruption of mast cells and the liberation therefrom of chemical mediators. However, this compound will lose its pharmacological effect when administered orally, and the extent to which this compound is applicable to naturally limited. Thus, the development of an antiallergic agent which can exhibit a sufficient therapeutic effect by oral administration has long been demanded in the field of medicine.

On the other hand, many compounds which have an N-acylaminobenzoic acid moiety and which might be considered to bear some distant resemblance to the compounds of this invention from the standpoint of chemical structure have been reported e.g., in Japanese Kokai No. 49-9,335, *J. Pharmacol.*, Vol. 58, pages 483-88, *Igakunoayumi*, Vol. 106, pages 576-85, *Liebig's Annalen der Chemie*, Vol. 341, pages 471-84, etc. In the above literatures or patents, it has been reported that some compounds, especially N-(3,4-dimethoxycinnamoyl) anthranilic acid, inhibit the disruption of mast cells and the release therefrom of chemical mediators caused by an antigen-antibody reaction and thus possess a strong antiallergic action when administered orally to mammals including human beings. However, such compounds do not have a substituent or substituents on their aromatic rings which contains amino and carboxyl groups. The compounds of this invention have one or more substituents on their aromatic rings which contains amino and carboxyl groups and exhibit a strong antiallergic action when administered orally.

SUMMARY OF THE INVENTION

An object of this invention is to provide new anthranilic acid derivatives possessing a pharmacological effect.

Another object of this invention is to provide anthranilic acid derivatives which exhibit a strong antiallergic action when administered to mammals.

Still another object of this invention is to provide anthranilic acid derivatives and the pharmaceutically acceptable salts thereof.

Yet another object of this invention is to provide antiallergic compositions comprising anthranilic acid derivatives or the pharmaceutically acceptable salts thereof.

Furthermore, another object of this invention is to provide methods for alleviating the diseases caused by allergies using the anthranilic acid derivatives or the pharmaceutically acceptable salts thereof.

Other objects, features and advantages of this invention will become apparent from the following description thereof.

Accordingly, the present invention provides anthranilic acid derivatives of the formula (I):

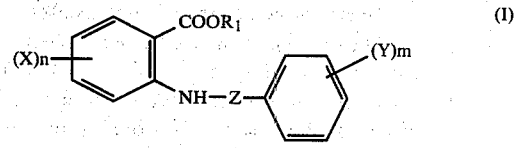

wherein X is a halogen atom, an alkoxyl group having 1-3 carbon atoms, an alkyl group having 1-3 carbon atoms or a nitro group, n is an integer of 1-2, Y is an alkoxyl group having 1-3 carbon atoms, m is an integer of 2-3, Z is $-COCH=CH-$ or $-CO-$, $R_1$ is a hydrogen atom or an alkyl group having 1-4 carbon atoms, and also provides the pharmaceutically acceptable salts thereof.

DETAILED DESCRIPTION OF THE INVENTION

The anthranilic acid derivatives of the general formula (I) of this invention can inhibit anaphylaxis, for example, inflammation of skin caused by an antigen-antibody reaction between reaginic antibody and its peculiar antigen, when administered orally. In view of their characteristic properties, it is expected that the compounds of this invention possess an antiallergic action and are effective for the therapeutical treatment of diseases caused by allergies, such as asthma, hay fever, urticaria and atopic dermatitis.

The compounds of the general formula (I) of this invention are characterized by the presence of a substituent or substituents on each aromatic ring, and those substituents play an important role in the antiallergic activity.

The substituents (X) on the aromatic ring which contains the amino and carboxyl groups can be selected from alkyl, alkoxyl and nitro groups and halogen atoms. In case the nuclear substituent (X) is an alkyl or alkoxyl group, the group has 1-3 carbon atoms. The halogen atom as a nuclear substituent (X) may be a chlorine atom, fluorine atom and bromine atom. In the substituent $(X)_n$, n is limited to one or two. Preferred examples of the nuclear substituent (X) include alkyl and alkoxyl groups and halogen atoms, and the most preferable nuclear substituent (X) is a halogen atom, especially a chlorine atom. The position of one or two substituents $(X)_n$ may be on any position, 1- or 2-position, preferably 4- or 5-position. The number n of the $(X)_n$ is preferably one.

On the other hand, the nuclear substituent (Y) may be a methoxy, ethoxy, propoxy or isopropoxy group, and a methoxy group is the most preferable among these alkoxyl groups. The number m of this nuclear substituents $(Y)_m$ is limited to 2-3. In general, the antiallergic action becomes stronger as the number m of the nuclear substituents $(Y)_m$ is greater and thus the number m of the substituents $(Y)_m$ is the most preferably 3.

Furthermore, the acyl group attached to the amino group of anthranilic acid, can be selected from benzoyl and cinnamoyl groups. In this case, the compounds having a cinnamoyl group tend to exhibit a stronger antiallergic activity than those having a benzoyl group.

The compounds of the general formula (I) of this invention in the form of an ester with an alkyl group having 1-4 carbon atoms also possess a strong antiallergic activity, however, these compounds tend to be slightly weak in antiallergic activity as compared with the corresponding compounds having a free acid group.

Salts of compounds of the general formula (I) of this invention having a carboxyl group, such as alkali metal salts, are as high in the pharmacological effect as the corresponding compounds having a free acid group.

Preferred compounds of this invention include
N-(3,4,5-trimethoxybenzoyl)-5-chloroanthranilic acid,
N-(3,4,5-trimethoxycinnamoyl)-5-chloroanthranilic acid,
N-(3,4-dimethoxycinnamoyl)-5-chloroanthranilic acid,
N-(3,4,5-trimethoxybenzoyl)-4-nitroanthranilic acid,
N-(3,4-dimethoxycinnamoyl)-5-methylanthranilic acid,
N-(3,4-dimethoxybenzoyl)-5-chloroanthranilic acid,
N-(3,4-dimethoxycinnamoyl)-4-chloroanthranilic acid,
N-(3,4,5-trimethoxybenzoyl)-5-iodoanthranilic acid,
N-(3,4,5-trimethoxycinnamoyl)-4-chloroanthranilic acid,
N-(3,4,5-trimethoxybenzoyl)-4-chloroanthranilic acid,
N-(3,4-dimethoxycinnamoyl)-4-fluoroanthranilic acid,
N-(3,4,5-trimethoxybenzoyl)-4-fluoroanthranilic acid,
N-(2,3,4-trimethoxycinnamoyl)-4-fluoroanthranilic acid,
N-(3,4-dimethoxycinnamoyl)-5-fluoroanthranilic acid,
N-(3,4,5-trimethoxybenzoyl)-6-chloroanthranilic acid,
N-(3,4-dimethoxycinnamoyl)-3-chloroanthranilic acid,
N-(3,4,5-trimethoxybenzoyl)-5-fluoroanthranilic acid,
N-(3,4,5-trimethoxybenzoyl)-3-chloroanthranilic acid
and their esters with an alkyl group having 1–4 carbon atoms.

More preferred compounds of this invention include
N-(3,4,5-trimethoxybenzoyl)-5-chloroanthranilic acid,
N-(3,4,5-trimethoxycinnamoyl)-5-chloroanthranilic acid,
N-(3,4-dimethoxybenzoyl)-5-chloroanthranilic acid,
N-(3,4-dimethoxycinnamoyl)-4-chloroanthranilic acid,
N-(3,4,5-trimethoxycinnamoyl)-4-chloroanthranilic acid,
N-(3,4,5-trimethoxybenzoyl)-6-chloroanthranilic acid and
N-(3,4,5-trimethoxybenzoyl)-4-fluoroanthranilic acid.

The most preferred compounds of this invention include
N-(3,4,5-trimethoxycinnamoyl)-5-chloroanthranilic acid,
N-(3,4,5-trimethoxycinnamoyl)-4-chloroanthranilic acid,
N-(3,4-dimethoxybenzoyl)-5-chloroanthranilic acid
and their esters with an alkyl group having 1–4 carbon atoms.

The compounds of the general formula (I) of this invention can be prepared, for example, by a process comprising reacting a reactive functional derivative of a compound of the general formula (II):

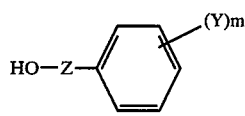

(II)

wherein Y is an alkoxyl group having 1–3 carbon atoms, m is an integer of 2–3, Z is —COCH=CH— or —CO—, with an anthranilic acid derivatives of the general formula (III):

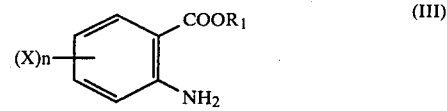

(III)

wherein X is a halogen atom, an alkoxyl group having 1–3 carbon atoms, an alkyl group having 1–3 carbon atoms or a nitro group, n is an integer of 1–2, $R_1$ is a hydrogen atom or an alkyl group having 1–4 carbon atoms, and then if desired, hydrolyzing the resulting compound.

The compounds of the general formula (II) above are known compounds and can easily be prepared according to methods disclosed in literature. Examples of the compounds of the general formula (II) above include cinnamic acid derivatives, such as 2,3-, 2,4-, 2,5-, 2,6-, 3,4- or 3,5-dimethoxycinnamic acid, 2,3-, 2,4-, 2,5-, 2,6-, 3,4- or 3,5-diethoxycinnamic acid, 2,3-, 2,4-, 2,5-, 2,6-, 3,4- or 3,5-dipropoxycinnamic acid, 2,3-, 2,4-, 2,5-, 2,6-, 3,4- or 3,5-diisopropoxycinnamic acid, 2,3,4-, 2,4,5- or 3,4,5-trimethoxycinnamic acid, 2,3,4-, 2,4,5- or 3,4,5-triethoxycinnamic acid, 2,3,4-, 2,4,5- or 3,4,5-tripropoxycinnamic acid and 2,3,4-, 2,4,5- or 3,4,5-triisopropoxycinnamic acid, 3-methoxy-4-ethoxycinnamic acid, 3-methoxy-4-propoxycinnamic acid, 4-methoxy-3-ethoxycinnamic acid, 4-methoxy-3-propoxycinnamic acid, 4-methoxy-3-isopropoxycinnamic acid, 3,5-dimethoxy-4-ethoxycinnamic acid and 3,5-dimethoxy-4-propoxycinnamic acid; and benzoic acid derivatives, such as 2,3-, 2,4-, 2,5-, 2,6-, 3,4- or 3,5-dimethoxybenzoic acid, 2,3-, 2,4-, 2,5-, 2,6-, 3,4- or 3,5-diethoxybenzoic acid, 2,3-, 2,4-, 2,5-, 2,6-, 3,4- or 3,5-dipropoxybenzoic acid, 2,3-, 2,4-, 2,5-, 2,6-, 3,4- or 3,5-diisopropoxybenzoic acid, 2,3,4-, 2,4,5- or 3,4,5-trimethoxybenzoic acid, 2,3,4-, 2,4,5- or 3,4,5-triethoxybenzoic acid, 2,3,4-, 2,4,5- or 3,4,5-triethoxybenzoic acid, 2,3,4- or 3,4,5-triisopropoxybenzoic acid, 3-methoxy-4-ethoxybenzoic acid, 3-methoxy-4-propoxybenzoic acid, 4-methoxy-3-ethoxybenzoic acid, 4-methoxy-3-propoxybenzoic acid, 4-methoxy-3-isopropoxybenzoic acid, 3,5-dimethoxy-4-ethylbenzoic acid and 3,5-dimethoxy-4-propoxybenzoic acid. The compounds of the general formula (II) above having an unsubstituted bond involve two isomers, i.e., cis-form and trans-form, and either may be employed for the purpose of this invention. In the process of this invention, reactive functional derivatives of these compounds are used as a starting material. Examples of the said derivatives include carboxylic acid derivatives such as acid halides, acid anhydrides, mixed acid anhydrides and esters. These reactive functional derivatives can easily be derived from the compounds of the general formula (II) according to the usual technique known in the art. For example, the acid chlorides can easily be obtained by refluxing for several hours the compound of the general formula (II) with thionyl chloride in the absence of any solvent or in benzene.

The anthranilic acid dervatives of the general formula (III) above are also known compounds and can easily be prepared according to methods disclosed in literature. Examples of the anthranilic acid derivatives of the general formula (III) include 3-, 4-, 5- or 6-chloroanthranilic acid, 3-, 4-, 5- or 6-iodoanthranilic acid, 3-, 4-, 5- or 6-bromoanthranilic acid, 4- or 5-fluoroanthranilic acid, 3-, 4-, 5- or 6-methylanthranilic acid, 3-, 4-, 5- or 6-methoxyanthranilic acid, 4-, 5- or 6-ethoxyanthranilic acid, 3-, 4-, 5- or 6-nitroanthranilic acid, 3,4-, 3,5-, 3,6- or 4,5-dichloroanthranilic acid, 3,5- or 4,5-dibromoanthranilic acid, 3,5- or 4,5-diiodoanthranilic acid, 3,5-dimethylanthranilic acid, 3,4- or 4,5-dimethoxyanthranilic acid 3,5- or 4,5-dinitroanthranilic acid and their esters with an alkyl group having 1-4 carbon atoms.

The above-mentioned amidation can be carried out according to methods per se. For example, when an acid halide is used as the reactive functional derivative, the acid halide can be reacted in an inert solvent with an anthranilic acid derivative of the general formula (III) in the presence of a basic substance. In this case, the basic substance used may be a tertiary organic base such as triethylamine, pyridine or N,N-dimethylpyridine or may also be an inorganic base such as sodium hydroxide, potassium hydroxide, sodium carbonate or potassium carbonate. Adequate as the inert solvent are chloroform, methylene chloride, acetone, benzene, toluene, tetrahydrofuran, dioxane and dimethylformamide.

The above process can be carried out preferably by dissolving an anthranilic acid derivative of the general formula (III) in a proportion of about 1 to about 1.5 mols per mol of an acid halide of the compound of the general formula (II) in a mixture of tetrahydrofuran and pyridine respectively in amounts of 5-20 times and 0.5-10 times as much as the amount of the compound of the general formula (II), adding a solution of an acid halide of the compound of the general formula (II) in tetrahydrofuran to the solution of the compound (III) under cooling and stirring, and then stirring the whole for several hours, and then if desired, refluxing the mixture for several hours.

The reaction mixture is concentrated under a reduced pressure to obtain a residue which is incorporated with water and, if desired, with an acid, for example, hydrochloric acid and the like, to make the mixture weakly acidic. The precipitated crystals are collected by filtration and then recrystallized from an adequate solvent to obtain the end product.

Furthermore, the compounds of the general formula (I) wherein R$_1$ is a hydrogen atom and Z is —COOH=CH—, can be prepared by reacting a compound of the general formula (IV):

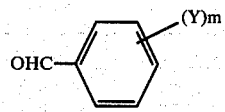

wherein Y and m have the same meanings as given above, in the presence of a condensing agent, with 2-methyl-3,1-benzoxazine-4-one derivatives of the general formula (V):

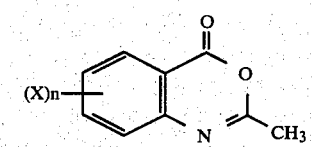

wherein X and n have the same meanings as given above, and hydrolyzing the resulting product to obtain the end product wherein R$_1$ is a hydrogen atom, and then if desired, esterifying the obtained compound according to usual techniques known in the art.

The compounds of the general formula (IV) above the known compounds and can be prepared according to methods disclosed in literature. The compounds of the general formula (IV) corresponding to the compounds of the general formula (II) can be employed for said methods. On the other hand, 2-methyl-3,1-benzoxazine-4-one derivatives of the general formula (V) above are known compounds and can be prepared by heating the anthranilic acid derivative of the general formula (III) above in acetic anhydride.

The condensing reaction described above in the reaction of a compound of the general formula (IV) with a 2-methyl-3,1-benzoxazine-4-one derivative of the general formula (V) can easily be carried out by the procedure as follows.

A compound of the general formula (IV) is heatd with 2-methyl-3,1-benzoxazine-4-one derivative of the general formula (V) in a proportion of about 1 to about 1.3 mols per mol of the compound of the general formula (IV) in the presence of an adequate amount of a condensing agent in an inert organic solvent, such as dioxane, tetrahydrofuran, benzene, toluene, etc., for about 30 minutes to about 5 hours at about 50° C. to about 150° C. Then the reaction mixture is cooled at room temperature, washed with water and dried, and then evaporated under a reduced pressure. Alternatively, the reaction mixture is evaporated under a reduced pressure. The residue is hydrolyzed in an aqueous alkali or acid solution at room temperature, and recrystallized to obtain the end product wherein R$_1$ is a hydrogen atom. This compound wherein R$_1$ is a hydrogen atom can easily be converted into the corresponding ester compound according to a usual manner.

Suitable examples of the condensing agent which can be used in the above reaction include phosphorus oxychloride, phosphorus, pentoxide, phosphorus trichloride, phosphorus tribromide, phosphorus pentabromide, polyphosphoric acid, polyphosphoric acid esters, benzenesulfonic acid, p-toluenesulfonic acid etc., and suitable amount of the condensing agent which can be used in the above reaction is from about 0.01 to about 1 mol per mol of the compound of the general formula (II).

The compound of the general formula (I) carrying a carboxyl group can be converted according to usual methods to a pharmaceutically acceptable salt thereof. For example, an aqueous solution of sodium bicarbonate in an equimolar amount can be added to an alcoholic solution of a compound of the general formula (I) and the mixture is warmed for an adequate period of time whereby the compound can easily be converted into its sodium salt. Suitable examples of the pharmaceutically acceptable salts include, in addition to sodium salts, potassium salts, magnesium salts, calcium salts, triethylammonium salts, and ammonium salts.

The compounds of the general formula (I) and the pharmaceutically acceptable salts thereof of the present invention can be administered to mammals including human beings by oral, intravenous, intramuscular or intrarectal administration, and when they are used, they are formulated into pharmaceutical compositions together with ordinary pharmaceutically acceptable carriers.

Various dosage forms of the therapeutic agents as an antiallergic agent can be selected according to the purpose of the therapy. Typical dosage forms which can be used are tablets, pills, powder, liquid preparations, suspensions, emulsions, granules, capsules, suppositories, and injectable preparations.

In molding the pharmaceutical composition into a tablet form, a wide variety of conventional carriers known in the art can be used. Examples of suitable carriers are excipients, such as glucose, lactose, starch, cacao butter, hardened vegetable oils, kaolin and talc, binders, such as gum arabic powder, tragacanth powder, gelatin, and ethanol, and disintegrants, such as laminaria and agar. The tablets, if desired, can be coated, and made into sugar-coated tablets, gelatin-coated tablets, enteric-coated tablets, film-coated tablets, or tablets coated with two or more layers.

When the pharmaceutical composition is formulated into an injectable preparation, the resulting solution and suspension are preferably sterilized, and are made isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into an antiallergic agent in an amount sufficient to prepare isotonic solutions. The therapeutic agent may further contain ordinary dissolving aids, buffers, pain-alleviating agents, and preservatives, and optionally coloring agents, perfumes, flavors, sweeteners, and other drugs.

The dosage of the compound of this invention is suitably selected according to the purpose of use, the symptoms, etc. Usually, a preferred dosage of the compound of this invention is about 5 to 20 mg/kg of body weight per day in multiple doses.

The anthranilic acid derivatives of this invention and the pharmaceutically acceptable salts thereof possess a special activity on the effects of an antigen-antibody reaction. Thus, they can be used widely as therapeutic medicaments for diseases caused by allergies.

This invention is further illustrated in more detail by way of the following examples.

EXAMPLE 1

To a solution of 1.7 g of 5-chloroanthranilic acid in 40 ml of pyridine is added a solution of 2.6 g of 3,4,5-trimethoxybenzoylchloride in tetrahydrofuran under cooling, and the mixture is stirred at room temperature for 2 hours and then heated to 80° C. for 30 minutes. The reaction mixture is concentrated under a reduced pressure and to the residue is added water. The precipitated crystals are recrystallized from acetone to obtain 1.4 g of N-(3,4,5-trimethoxybenzoyl)-5-chloroanthranilic acid as colorless needles.

Melting point: 273°–275° C.

| | Elemental analysis as $C_{17}H_{16}ClNO_6$ | | |
|---|---|---|---|
| | C % | H % | N % |
| Calcd. | 55.82 | 4.41 | 3.83 |
| Found | 55.79 | 4.38 | 3.75 |

EXAMPLE 2

In a mixture of 30 ml of chloroform and 3 ml of triethylamine is dissolved 3.4 g of 5-chloroanthranilic acid. To this solution is added a solution of 4.5 g of 3,4-dimethoxycinnamoylchloride in chloroform, and the mixture is heated under reflux for 2 hours. The reaction mixture is concentrated under a reduced pressure, and to the residue is added water and hydrochloric acid then added to make the mixture weakly acidic. The precipitated crystals are collected by filtration and recrystallized from ethanol to obtain 3.1 g of N-(3,4-dimethoxycinnamoyl)-5-chloroanthranilic acid as pale yellow needles.

Melting point: 210°–213° C.

| | Elemental analysis as $C_{18}H_{16}ClNO_5$ | | |
|---|---|---|---|
| | C % | H % | N % |
| Calcd. | 59.76 | 4.46 | 3.88 |
| Found | 59.52 | 4.38 | 3.86 |

EXAMPLE 3

To a solution of 1.3 g of methyl 5-chloroanthranilate and 1.8 g of 3,4,5-trimethoxybenzoylchloride in 30 ml of tetrahydrofuran is added 1.5 g of triethylamine under cooling, and the mixture is stirred at room temperature for 2 hours and then heated under reflux for 1 hour. The reaction mixture is concentrated under reduced pressure and to the residue is added water. The precipitated crystals are collected by filtration and recrystallized from a mixture of chloroform and ether to obtain 1.4 g of methyl N-(3,4,5-trimethoxybenzoyl)-5-chloroanthranilate as colorless prisms.

Melting point: 179°–180° C.

| | Elemental analysis as $C_{18}H_{18}ClNO_5$ | | |
|---|---|---|---|
| | C % | H % | N % |
| Calcd. | 59.42 | 4.99 | 3.85 |
| Found | 59.22 | 5.17 | 3.72 |

To a solution of 20 ml of a 10% aqueous solution of sodium hydroxide and 10 ml of ethanol is added 0.95 g of methyl N-(3,4,5-trimethoxybenzoyl)-5-chloroanthranilate and the mixture is stirred at room temperature for 1 hour. The reaction mixture is poured into 100 ml of water and after cooling, hydrochloric acid is added to make the mixture weakly acidic. The precipitated crystals are collected by filtration and recrystallized from ethanol to obtain 0.7 g of N-(3,4,5-trimethoxybenzoyl)-5-chloroanthranilic acid as colorless needles.

Melting point: 273°–275° C.

In a similar manner, the following compounds can be prepared:

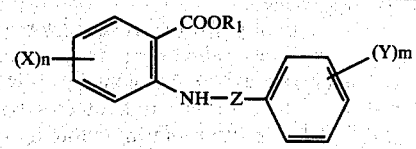

| Comp No. | m | Y | Z | n | X | $R_1$ | M.P. °C. |
|---|---|---|---|---|---|---|---|
| 1 | 3 | 3-OMe, 4-OMe, 5-OMe | —COCH=CH— | 1 | 5-Cl | H | 223–224 |
| 2 | 3 | 3-OMe, 4-OMe, 5-OMe | —CO— | 1 | 5-Cl | $C_2H_5$ | 158–160 |
| 3 | 3 | 3-OMe, 4-OMe, 5-OMe | —COCH=CH— | 1 | 5-Cl | $CH_3$ | 174–176 |
| 4 | 2 | 3-OMe, 4-OMe | —COCH=CH— | 1 | 5-Cl | $CH_3$ | 197–198 |

EXAMPLE 4

In a mixture of 3.2 g of methyl 4,5-dimethoxyanthranilate in 30 ml of chloroform is dissolved 3 ml of triethylamine, and to this solution is added a solution of 3.45 g of 3,4,5-trimethoxybenzoylchloride in chloroform under cooling. The mixture is stirred at room temperature for 4 hours. The reaction mixture is concentrated under a reduced pressure and to the residue is added water. The precipitated crystals are recrystallized from a mixture of dimethylformamide and ethanol to obtain 4.8 g of methyl N-(3,4,5-trimethoxybenzoyl)-4,5-dimethoxyanthranilate as pale yellow prisms.

Melting point: 181°–183° C.

| | Elemental analysis as $C_{20}H_{23}NO_8$ | | |
|---|---|---|---|
| | C % | H % | N % |
| Calcd. | 59.25 | 5.72 | 3.46 |
| Found | 59.31 | 5.69 | 3.38 |

EXAMPLE 5

In a mixture of 3 g of 5-methylanthranilic acid in 30 ml of chloroform is dissolved 3 ml of triethylamine, to this mixture is added a solution of 4.2 g of 3,4-dimethoxycinnamoylchloride in chloroform under cooling. The mixture is stirred at room temperature for 2 hours and then heated under reflux for 2 hours. The reaction mixture is concentrated under a reduced pressure, to the residue is added water and hydrochloric acid is added to make the mixture the weakly acidic. The precipitated crystals are collected by filtration recrystallized from ethanol to obtain 4.8 g of N-(3,4-dimethoxycinnamoyl)-5-methylanthranilic acid as pale yellow needles.

Melting point: 190°–191° C.

| | Elemental analysis as $C_{19}H_{19}NO_5$ | | |
|---|---|---|---|
| | C % | H % | N % |
| Calcd. | 66.85 | 5.61 | 4.10 |
| Found | 66.81 | 5.74 | 4.06 |

In a similar manner, the following compounds can be prepared:

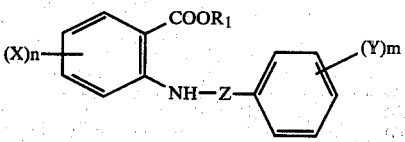

| Comp No. | m | Y | Z | n | X | $R_1$ | M.P. °C. |
|---|---|---|---|---|---|---|---|
| 5 | 3 | 3-OMe, 4-OMe, 5-OMe | —CO— | 2 | 4-OMe, 5-OMe | H | 276–277 |
| 6 | 2 | 3-OMe, 4-OMe | —COCH=CH— | 2 | 4-OMe, 5-OMe | H | 254–255 |
| 7 | 3 | 3-OMe, 4-OMe, 5-OMe | —CO— | 1 | 4-$NO_2$ | H | 266–268 |
| 8 | 3 | 3-OMe, 4-OMe, 5-OMe | —CO— | 1 | 5-$NO_2$ | H | 290–293 |
| 9 | 2 | 3-OMe, 4-OMe | —COCH=CH— | 1 | 4-$NO_2$ | H | 240–243 |
| 10 | 3 | 3-OMe, 4-OMe, 5-OMe | —CO— | 1 | 5-Me | H | 246–247 |
| 11 | 3 | 3-OMe, 4-OMe, 5-OMe | —CO— | 1 | 5-Me | $CH_3$ | 144–145 |
| 12 | 2 | 3-OMe, 4-OMe | —COCH=CH— | 2 | 4-OMe, 5-OMe | $CH_3$ | 203–204 |

EXAMPLE 6

In a mixture of 3.4 g of 4-chloroanthranilic acid in 50 ml of tetrahydrofuran is dissolved 3 ml of triethylamine, to this mixture is added slowly a solution of 4.5 g of 3,4-dimethoxycinnamoylchloride in tetrahydrofuran under room temperature, and this solution is stirred at room temperature for 5 hours. The reaction mixture is concentrated under a reduced pressure, to the residue is added water and hydrochloric acid is added to make the mixture the weakly acidic. The precipitated crystals are collected by filtration and recrystallized from a mixture of dimethylformamide and water to obtain 5.9 g of N-(3,4-dimethoxycinnamoyl)-4-chloroanthranilic acid as colorless prisms.

Melting point: 255°–257° C.

| | Elemental analysis as $C_{18}H_{16}ClNO_5$ | | |
|---|---|---|---|
| | C % | H % | N % |
| Calcd. | 59.76 | 4.46 | 3.87 |
| Found | 59.73 | 4.51 | 3.81 |

EXAMPLE 7

In a mixture of 20 ml of tetrahydrofuran and 1.6 g of dimethylaniline is dissolved 1.6 g of 4-fluoroanthranilic acid. To this solution is added slowly a solution of 2.3 g of 3,4,5-trimethoxybenzoylchloride in tetrahydrofuran under room temperature and the mixture is strred at room temperature for 5 hours. The reaction mixture is concentrated under a reduced pressure, to the residue is added water and hydrochloric acid is added to make the mixture the weakly acidic. The precipitated crystals are collected by filtration and recrystallized from methanol to obtain 2.1 g of N-(3,4,5-trimethoxybenzoyl)-4-fluoroanthranilic acid as colorless needles.

Melting point: 232°–233° C.

|  | Elemental analysis as $C_{17}H_{16}FNO_6$ | | |
|---|---|---|---|
|  | C % | H % | N % |
| Calcd. | 58.45 | 4.62 | 4.01 |
| Found | 58.41 | 4.56 | 4.08 |

In a similar manner, the following compounds can be prepared:

An anti-DNP-As rat serum, antibody, was prepared by this antigen.

This antibody with sufficient titer was injected into the three sites of the dorsal shaved skin, and to check the experimental error, saline (0.1 ml/site) was also injected into another three sites of the dorsal shaved skin. 48 hours after the injection, 1 ml of an antigen solution containing 0.25% Evans blue (2 mg of protein content) was injected intravenously. The animals were exsanguinated 30 minutes after challenge with the antigen. The area blued as a result of PCA (Passive Cutaneous Anaphylaxis) was excised and measured. The amount of dye leaked was determined according to the method of Harada, M., et al. (Harada, M., et al., J. Pharm. Pharmacol., 23, 218, 1971).

A given test compound was administered intraperitoneally at a dose of 100 mg/kg 30 minutes before the challenge of the antigen. Disodium chromoglicate (DSCG) and N-(3,4-dimethoxycinnamoyl)-anthranilic

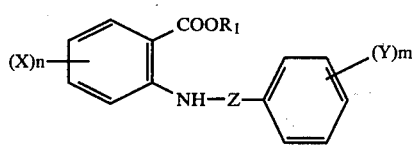

| Comp No. | m | Y | Z | n | X | $R_1$ | M.P. °C. |
|---|---|---|---|---|---|---|---|
| 13 | 2 | 3-OMe, 4-OMe | —COCH=CH— | 1 | 5-F | H | 217–219 |
| 14 | 3 | 2-OMe, 3-OMe, 4-OMe | —COCH=CH— | 1 | 5-Cl | H | 213–215 |
| 15 | 3 | 3-OMe, 4-OMe, 5-OMe | —COCH=CH— | 1 | 4-Cl | H | 228–231 |
| 16 | 2 | 3-OMe, 4-OMe | —COCH=CH— | 1 | 4-F | H | 232–234 |
| 17 | 3 | 3-OMe, 4-OMe, 5-OMe | —CO— | 1 | 5-F | H | 271–272 |
| 18 | 3 | 3-OMe, 4-OMe, 5-OMe | —CO— | 1 | 5-I | H | 275–277 |
| 19 | 2 | 3-OMe, 4-OMe | —COCH=CH— | 1 | 5-I | H | 231–233 |
| 20 | 3 | 2-OMe, 3-OMe, 4-OMe | —COCH=CH— | 1 | 5-Cl | $CH_3$ | 135–137 |
| 21 | 3 | 2-OMe, 3-OMe, 4-OMe | —COCH=CH— | 1 | 4-F | H | 237–239 |
| 22 | 3 | 3-OMe, 4-OMe, 5-OMe | —CO— | 1 | 6-Cl | H | 215–217 |
| 23 | 3 | 3-OMe, 4-OMe, 5-OMe | —CO— | 1 | 3-Cl | H | 226–228 |
| 24 | 2 | 3-OMe, 4-OMe | —COCH=CH— | 2 | 3-Cl, 5-Cl | H | 210–213 |
| 25 | 2 | 3-OMe, 4-OMe | —COCH=CH— | 1 | 3-Cl | H | 202–203 |

EXAMPLE 8

In 300 ml of an aqueous alcoholic solution (ethanol 1:water 1) containing 0.4 g of sodium hydroxide is added 3.6 g of N-(3,4-dimethoxycinnamoyl)-4-chloroanthranilic acid and the mixture is warmed to be completely dissolved. The solution is concentrated under a reduced pressure, the residue is dissolved in 200 ml of warmed ethanol and to this solution is added 900 ml of ether. The precipitated crystals are collected by filtration and dried under reduced pressure to obtain 3.2 g of sodium N-(3,4-dimethoxycinnamoyl)-4-chloroanthranilate.

Melting point: 290°–292° C. (decomp)

EXAMPLE 9

HOMOLOGOUS PASSIVE CUTANEOUS ANAPHYLAXIS IN RATS

Inhibitory potency of anthranilic acid derivatives on Homologous Passive Cutaneous Anaphylaxis in rats was measured by the method of Tada, T et al. (J. Immunol., 106, 1002, 1971). Wistar male rats weighing 170–190 g were used in this experiment.

An antigen, DNP-As (Dinitrophenyl coupled Ascaris suum extract), was prepared by coupling dinitrophenol and Ascaris suum extract.

acid (N-5') were used for comparison.

| Compound | Dye area (mm$^2$) | Inhibition (%) | Amount of dye (μg) | Inhibition (%) |
|---|---|---|---|---|
| control (no active ingredient used) | 63.7 ± 4.0 | — | 9.6 ± 1.8 | — |
| DSCG | 43.6 ± 3.5 | 31.6 | 6.3 ± 1.2 | 34.4 |
| N-5' | 44.6 ± 3.7 | 30.0 | 7.2 ± 1.2 | 25.0 |
| comp. of Example 1 | 27.5 ± 3.8 | 56.8 | 4.8 ± 1.2 | 50.0 |

FORMULATION EXAMPLE 1

100 g of N-(3,4,5-trimethoxycinnamoyl)-5-chloroanthranilic acid was admixed with 600 g of lactose and 1,400 g of Indian corn starch and then with 7,000 ml of a 5% aqueous solution of hydroxypropylcellulose. The mixture was kneaded and then pills were produced therefrom. Next, the pills were admixed with 100 g of calcium carboxymethylcellulose and 50 g of calcium stearate and 1,000 tablets were produced from the mixture.

FORMULATION EXAMPLE 2

| | |
|---|---|
| N-(3,4,5-trimethoxycinnamoyl)-5-chloroanthranilic acid | 200 g |
| Corn Starch | 70 g |
| Magnesium Stearate | 2 g |
| Hydroxymethyl cellulose | 10 g |
| Macrogol 6000 | 3 g |
| Castor Oil | 40 g |
| Ethanol | 40 g |

N-(3,4,5-trimethoxycinnamoyl)-5-chloroanthranilic acid, the corn starch and the magnesium stearate were mixed and ground, and then tableted using a conventional pounder for sugar coating.

The resulting tablets were coated with a film coating agent composed of hydroxymethyl cellulose, macrogol 6000, castor oil and ethanol to produce film coated tablets.

FORMULATION EXAMPLE 3

Tablets each containing 100 mg of an active ingredient were prepared from the following compositions.

| | |
|---|---|
| N-(3,4,5-trimethoxycinnamoyl)-5-chloroanthranilic acid | 100.0 mg |
| Lactose | 64.0 mg |
| Starch | 19.4 mg |
| Microcrystalline cellulose | 20.0 mg |
| Talc | 5.0 mg |
| Methylcellulose | 0.6 mg |
| Magnesium Stearate | 1.0 mg |
| | 210.0 mg |

While the invention has been described in detail and with reference to specific embodiments thereof, it will be apparent to one skilled in the art that various changes and modifications can be made therein without departing from the spirit and scope thereof.

What is claimed is:

1. A compound of the general formula (I):

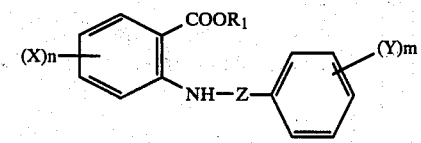

wherein X is a halogen atom, an alkoxyl group having 1-3 carbon atoms, an alkyl group having 1-3 carbon atoms or a nitro group, n is an integer of 1-2, Y is an alkoxyl group having 1-3 carbon atoms, m is an integer of 2-3, Z is $-COCH=CH-$, $R_1$ is a hydrogen atom or an alkyl group having 1-4 carbon atoms, and pharmaceutically acceptable salts thereof.

2. A compound of the general formula (I):

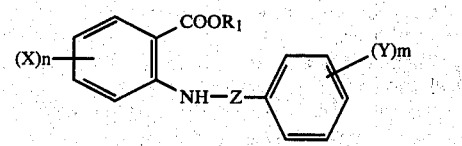

wherein X is a halogen atom, a methoxy group or a nitro group, n is an integer of 1-2, Y is a methoxy group, m is an integer of 2-3, Z is $-COCH=CH-$, $R_1$ is a hydrogen atom or a methyl group, and pharmaceutically acceptable salts thereof.

3. A compound according to claim 2, wherein X is a halogen atom.

4. A compound according to claim 3, wherein n is 1.

5. A compound according to claim 4, wherein Y is a methoxy group.

6. The compound as claimed in claim 3 of the formula:

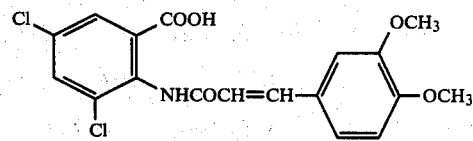

7. The compound as claimed in claim 5 of the formula:

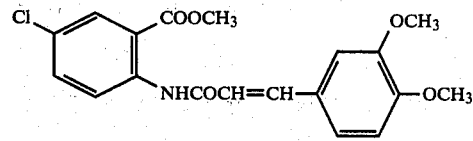

8. The compound as claimed in claim 5 of the formula:

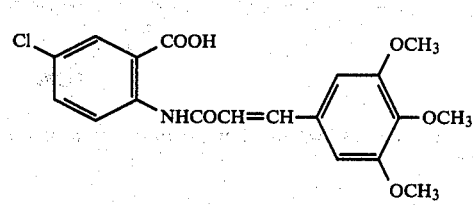

9. The compound as claimed in claim 5 of the formula:

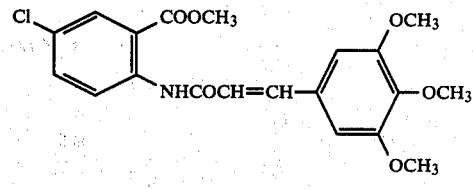

10. The compound as claimed in claim 5 of the formula:

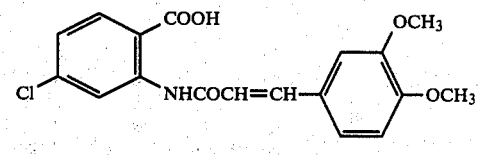

11. The compound as claimed in claim 5 of the formula:

12. The compound as claimed in claim 5 of the formula:

4-F-C6H3(COOH)-NHCOCH=CH-C6H3(OCH3)(OCH3)

13. The compound as claimed in claim 5 of the formula:

Cl-C6H3(COOH)-NHCOCH=CH-C6H2(OCH3)(OCH3)(OCH3)

14. The compound as claimed in claim 5 of the formula:

Cl-C6H3(COOCH3)-NHCOCH=CH-C6H2(OCH3)(OCH3)(OCH3)

15. The compound as claimed in claim 5 of the formula:

Cl-C6H3(COOH)-NHCOCH=CH-C6H2(OCH3)(OCH3)(OCH3)

16. The compound as claimed in claim 5 of the formula:

F-C6H3(COOH)-NHCOCH=CH-C6H3(OCH3)(OCH3)

17. The compound as claimed in claim 5 of the formula:

I-C6H3(COOH)-NHCOCH=CH-C6H3(OCH3)(OCH3)

F-C6H3(COOH)-NHCOCH=CH-C6H2(OCH3)(OCH3)(OCH3)

18. The compound as claimed in claim 5 of the formula:

Cl-C6H3(COOH)-NHCOCH=CH-C6H3(OCH3)(OCH3)

19. The compound as claimed in claim 5 of the formula:

Cl-C6H3(COOH)-NHCOCH=CH-C6H3(OCH3)(OCH3)

20. The compound as claimed in claim 2 of the formula:

$O_2N$-C6H3(COOH)-NHCOCH=CH-C6H3(OCH3)(OCH3)

21. The compound as claimed in claim 2 of the formula:

$H_3CO$-C6H2($H_3CO$)(COOH)-NHCOCH=CH-C6H3(OCH3)(OCH3)

22. The compound as claimed in claim 2 of the formula:

$H_3CO$-C6H2($H_3CO$)(COOCH3)-NHCOCH=CH-C6H3(OCH3)(OCH3)

23. The compound as claimed in claim 1 of the formula:

$H_3C$-C6H3(COOH)-NHCOCH=CH-C6H3(OCH3)(OCH3)

24. An antiallergic composition comprising a therapeutically effective amount of at least one compound of the general formula (I) according to claim 1 and one or more pharmaceutically acceptable carriers or diluents.

25. A method of alleviating diseases caused by allergies, such as asthma, hay fever, urticaria and atopic dermatitis, comprising administering a therapeutically effective amount of at least one compound of the general formula (I), according to claim 1 to a subject afflicted with said diseases.

* * * * *